(12) United States Patent
Hansson

(10) Patent No.: US 9,308,032 B2
(45) Date of Patent: Apr. 12, 2016

(54) DEVICE FOR FIXATION OF BONE FRAGMENTS AT BONE FRACTURES

(76) Inventor: Henrik Hansson, Vreta Kloster (SE)

( * ) Notice: Subject to any disclaimer, the term of this patent is extended or adjusted under 35 U.S.C. 154(b) by 1369 days.

(21) Appl. No.: 12/670,147

(22) PCT Filed: Jul. 8, 2008

(86) PCT No.: PCT/SE2008/050847
§ 371 (c)(1),
(2), (4) Date: May 5, 2010

(87) PCT Pub. No.: WO2009/014484
PCT Pub. Date: Jan. 29, 2009

(65) Prior Publication Data
US 2010/0280556 A1    Nov. 4, 2010

(30) Foreign Application Priority Data
Jul. 24, 2007  (SE) ...................................... 0701775

(51) Int. Cl.
*A61B 17/80* (2006.01)
*A61B 17/74* (2006.01)
*A61B 17/72* (2006.01)

(52) U.S. Cl.
CPC .......... *A61B 17/746* (2013.01); *A61B 17/7266* (2013.01)

(58) Field of Classification Search
USPC .............................. 606/286, 289–291, 64–67
See application file for complete search history.

(56) References Cited

U.S. PATENT DOCUMENTS 2,627,855 A    4/1950 Price
5,324,292 A    6/1994 Meyers
5,591,168 A    1/1997 Judet et al.
5,976,139 A *  11/1999 Bramlet ......................... 606/66
6,468,278 B1   10/2002 Muckter (Continued)

FOREIGN PATENT DOCUMENTS

EP         0 274 713         12/1987
WO      2004/049963          6/2004
WO   WO-2004/049953 A1       6/2004

(Continued)

*Primary Examiner* — David Bates
*Assistant Examiner* — Olivia C Chang
(74) *Attorney, Agent, or Firm* — Tarolli, Sundheim, Covell & Tummino LLP

(57) ABSTRACT

The present invention relates to a device for fixation of bone fragments at bone fractures. The device comprises at least two fixation means (1), a securing plate (17), and a securing means for the respective fixation means with a view to achieving a stable rigid connection between fixation means (1) and the securing plate (17) and configuring the device in such a way that the fixation means are not allowed to change their angular position relative to the securing plate and relative to one another, each fixation means (1) has a first fixing portion (9) for fixing the fixation means in an inner bone fragment (3), a second fixing portion for locking the fixation means, which involves using the securing means, to the securing plate (17) which is disposed on the outside of an outer bone fragment (2) and allows movement of the outer bone fragment relative to it, so that the fixation means are prevented from changing their angular position relative to the securing plate and relative to one another, and a middle portion (32) which is situated between the fixing portions and runs through the outer bone fragment, along which middle portion the outer bone fragment can slide inwards towards the inner bone fragment in which the fixation means is fixed.

9 Claims, 3 Drawing Sheets

(56) References Cited

U.S. PATENT DOCUMENTS

2004/0181222 A1* 9/2004 Culbert et al. .................. 606/60
2007/0055248 A1 3/2007 Zlowodzki et al.

FOREIGN PATENT DOCUMENTS

| WO | WO-2004/064603 A2 | 8/2004 |
| WO | 2004/075766 | 9/2004 |

* cited by examiner

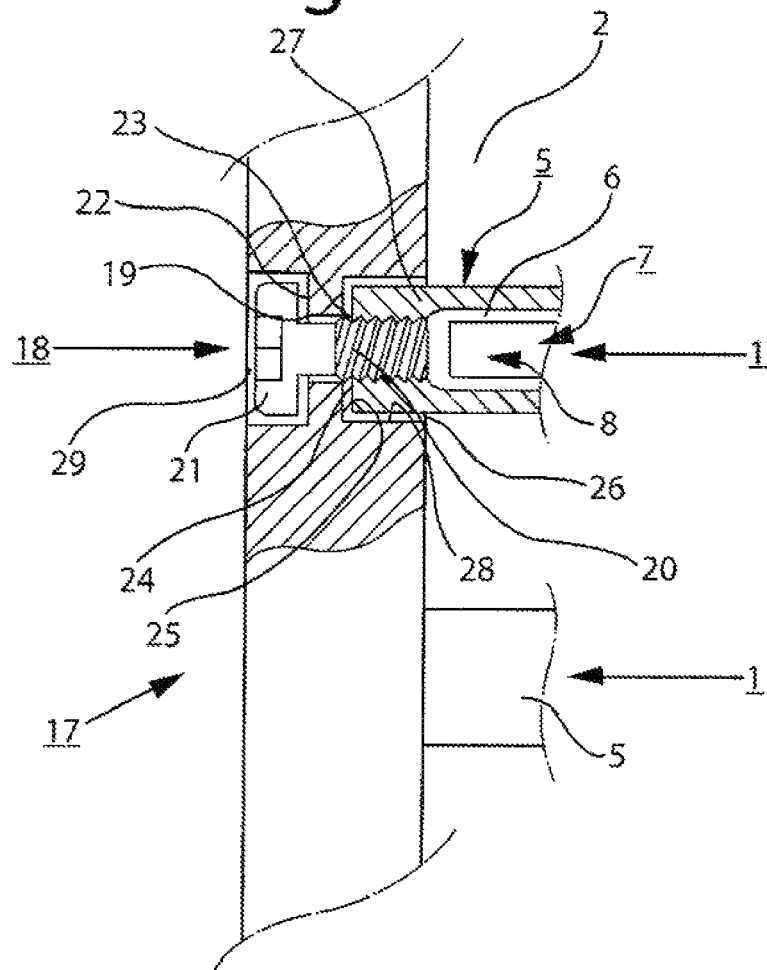
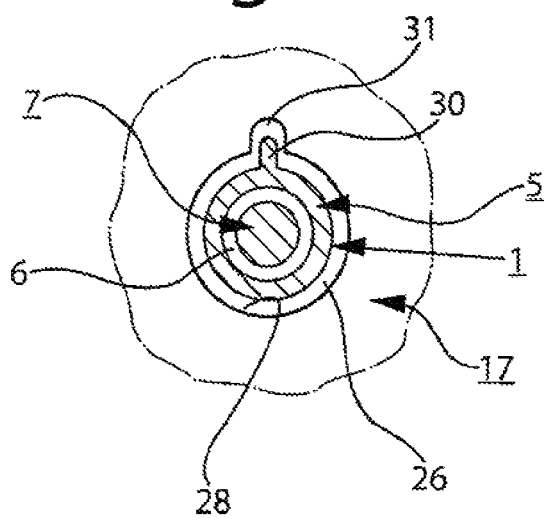

DEVICE FOR FIXATION OF BONE FRAGMENTS AT BONE FRACTURES

BACKGROUND TO THE INVENTION

The present invention relates to a device for fixation of bone fragments at bone fractures. The device comprises at least two fixation means, a securing plate and a securing means for the respective fixation means.

After a bone fracture such as a femur neck fracture, the bone fragments at the fracture need fixing. This is currently done by using suitable fixation means, e.g. bone nails or bone screws.

After the completion of surgery, even as early as when the effects of the anaesthesia have passed and the patient is still confined to bed, but above all when the patient is beginning to be up and walk and stand on the leg, the fixed bone fragments and the fixation means are subject to large forces, particularly to rotational forces downwards and rearwards.

The fixation means alone are often insufficient to counteract these rotational forces and the bone fragments have to be used to help to lock the fracture. If this is not done and the bone fragments are caused to rotate relative to one another by said forces, the result will be shifting of the angular positions of the fixation means to such an extent that they risk substantially crossing one another, thereby keeping the fracture parted and preventing healing.

BRIEF SUMMARY OF THE INVENTION

The object of the present invention is accordingly to prevent or counteract this and therefore configure the device in such a way that the fixation means are not allowed to rotate and cross one another.

To this end, with the device according to the invention, each fixation means has a first fixing portion for fixing the fixation means in an inner bone fragment, a second fixing portion for locking the fixation means, which involves using the securing means, to the securing plate disposed on the outside of an outer bone fragment and allowing movement of the outer bone fragment relative to it, so that the fixation means are prevented from changing their angular position relative to the securing plate and relative to one another, and a middle portion which is situated between the fixing portions and runs through the outer bone fragment, along which middle portion the outer bone fragment can slide inwards towards the inner bone fragment in which the fixation means is fixed.

The result of the fixation means being thus fixed in the inner bone fragment and to the securing plate while the outer bone fragment can move towards the inner bone fragment and, in so doing, be guided by the fixation means is that the bone fragments are kept fixed but compression of the bone fragments is nevertheless allowed, the device and the bone fragments thus being able to absorb the aforesaid rotational forces and control them so that no redislocation occurs.

Other objects and advantages of the invention will be apparent to one skilled in the art who examines the attached drawings and the following detailed description of preferred embodiments.

BRIEF DESCRIPTION OF THE DRAWINGS

FIG. 3 is a schematic longitudinal section through rear portions of a fixation means and through a securing plate and a securing means which also form part of the device according to the present invention; and FIG. 4 is a schematic view in cross-section through an alternative version of a fixation means and of a securing plate which also forms part of the device according to the present invention.

DETAILED DESCRIPTION OF PREFERRED EMBODIMENTS OF THE INVENTION

Figure 1:
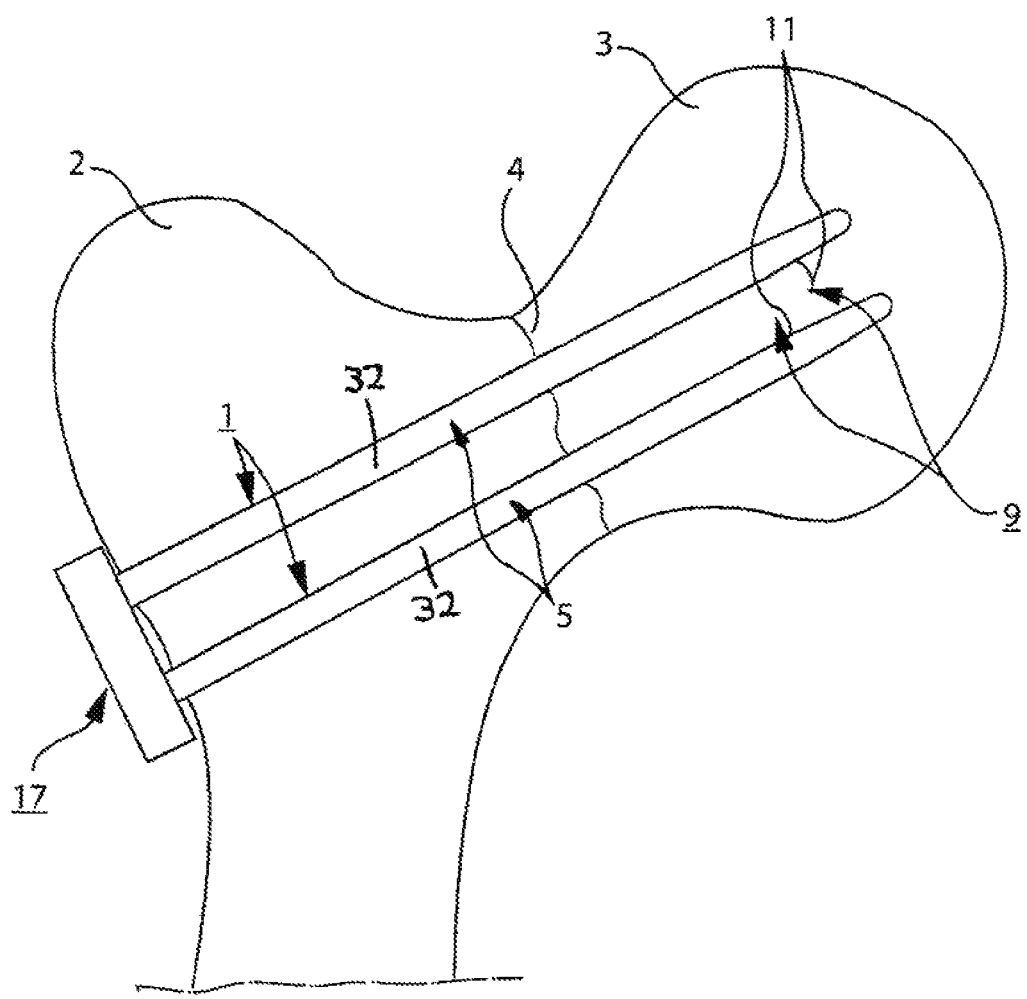
FIG. 1 is a schematic longitudinal section through upper portions of a femur with a fracture at the neck of the femur and provided with a device according to the present invention.

FIG. 1 depicts two substantially parallel fixation means 1 for fixing bone fragments 2 and 3 at a femur neck fracture 4. The number of fixation means may vary, as also the type of bone fracture at which bone fragments have to be fixed. Each fixation means 1 is configured for insertion through an outer bone fragment 2 and fixing to an inner bone fragment 3.

The fixation means 1 may be of any suitable type for the intended purpose and function. It may for example take the form of a bone screw or, as in the version depicted, a bone nail 1 which has a preferably cylindrical sleeve 5 with a longitudinal space 6 which is open rearwards for insertion of a pin 7 which is preferably cylindrical at least rearwards, with an outside diameter at least partly adapted to the inside diameter of the sleeve. This pin 7 is movable in the longitudinal direction of the sleeve 5 and has a rear portion 8 and at least one forward portion 9 which extends forward from the rear portion. The forward portion 9 has at its front end a curved tip 11.

Forward portions of the sleeve 5 have at least one aperture 13 on a side of the sleeve. The forward portion 9 of the pin 7 can be driven through the side aperture 13 outwards from the sleeve 5 by the pin being driven forwards relative to the sleeve. This driving of the pin 7 forwards relative to the sleeve 5 may be effected by using a suitable type of driving tool (not depicted).

The space of the sleeve 5 ends forwards with at least one guide surface 15 directed obliquely forwards/outwards relative to a centreline CL which runs in a longitudinal direction through the space 6 of the sleeve and thus constitutes the longitudinal axis of the fixation means.

In a state of readiness (not depicted) in which the pin 7 is inserted in the sleeve 5, the tip 11 of the pin abuts against or is situated close to the guide surface 15.

Figure 2:
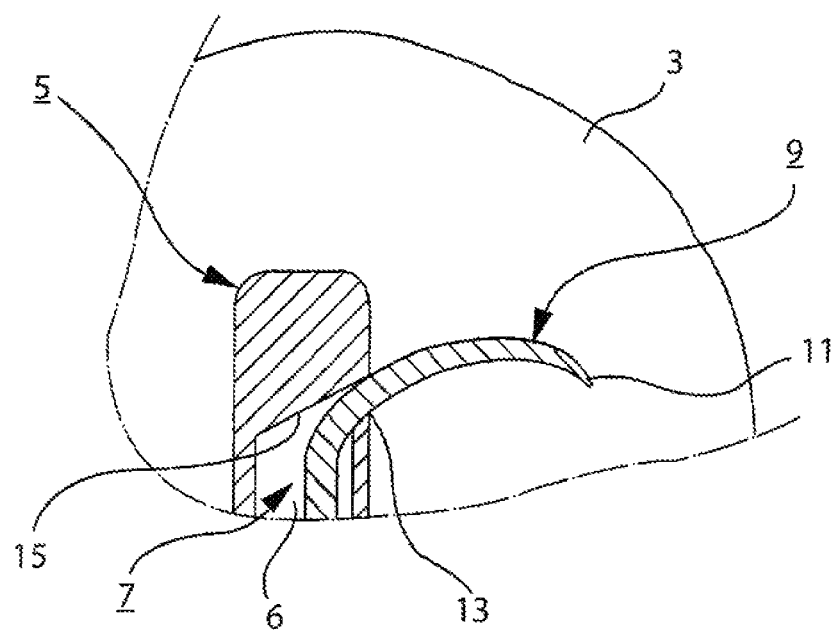
FIG. 2 is a schematic longitudinal section through portions of the head of the femur and forward portions of a fixation means.

In the version depicted, when holes for the respective fixation means 1 have been drilled through the outer bone fragment 2 and into the inner bone fragment 3 at the femur neck fracture 4 and the fixation means have been introduced into the holes, the pin 7 is driven outwards from the sleeve 5. During the driving of the pin 7 forwards relative to the sleeve 5, the guide surface 15 will guide the forward portion 9 of the pin outwards through the side aperture 13, said forward portion forming a hook which engages in the inner bone fragment 3 (see FIG. 2). This hook 9 may be referred to as the first fixing portion of the fixation means 1.

As the density in the inner bone fragment 3 is greatest at its centre, it is of advantage if the respective fixation means 1 are applied and/or configured in such a way that, during the driving, the forward portion 9 of the pin 7 is caused to engage in the central portions of the bone fragment. The fact that the forward portion 9 of the pin 7 in the respective points towards the centre of the inner bone fragment 3 means not only that the fixation means have a better grip in this inner bone fragment but also that the risk of rotation and other movements of the fixation means is counteracted.

After the driving of the forward portion 9 of the pin 7 into the inner bone fragment 3, a securing plate 17 is disposed at rear portions of the fixation means 1 which protrude from the outer bone fragment 2. These protruding rear portions may be referred to as the second fixing portion of the fixation means 1. The securing plate 17 is configured to secure the respective fixation means 1 on an outside of the outer bone fragment 2. The securing plate 17 is so configured that it allows movement of the outer bone fragment 2 relative to it, i.e. it is not connected to the outer bone fragment nor disposed in some other way whereby it would have moved with the latter upon compression of the bone fragments 2, 3.

A securing means 18 for the respective fixation means 1 is thereafter placed in position, which securing means is configured to secure the fixation means to the securing plate 17.

According to the present invention, the rear portions of the respective fixation means 1, the securing plate 17, and the securing means 18 are configured to draw the respective fixation means 1 firmly against the securing plate so that the fixation means is prevented from changing its angular position relative to the securing plate and relative to other fixation means.

FIG. 3 depicts the respective securing means preferably in the form of a screw 18. The securing plate 17 has a hole 19 through which a threaded portion 20 of the screw 18 is insertable until a head 21 of the screw abuts against the surface 22 of the securing plate. The orientation of the hole 19 depends on how the fixation means 1 runs relative to the securing plate 17. The respective fixation means 1 has at its said rear portions a threaded hole 23 in which the threaded portion 20 of the screw 18 is screwable so that when the screw is screwed into the threaded hole of the fixation means, the fixation means is drawn towards the securing plate 17 until a rear surface 24 on the fixation means, i.e. on the rear portions of the fixation means, abuts against a bearing surface 25 on the securing plate. The threaded connection results in good rotationally firm and immovable fixing of the respective fixation means 1 to the securing plate 17 and hence good fixation of the femur neck fracture.

The fixing of the respective fixation means 1 to the securing plate 17 is further improved by a version of the device according to the present invention in which the securing plate has a recess 26 for the rear portions of the respective fixation means 1, i.e. primarily rear portions 27 of the sleeve 5 (see FIG. 3). A bottom of the respective recess 26 constitutes the bearing surface 25 against which the rear surface 24 of the fixation means 1 is tightenable. The diameter or equivalent of the respective recess 26 and the diameter or equivalent of the rear portions 27 of the respective fixation means 1 are mutually so adapted that said rear portions fit into the recess with substantially no play between them. Accordingly, sidewalls 28 in the respective recess 26 substantially prevent the rear portions 27 of the fixation means 1 which engage in the recess from changing their angular position relative to the securing plate 17 and relative to other fixation means. With advantage, the securing plate 17 also has a recess 29 for the respective securing means 18, the bottom of which recess constitutes said surface 22 for the abutment of the screw head 21.

FIG. 4 depicts another alternative version of the device according to the present invention. In this case, the fixation means 1 comprises, as at least part of said second fixing portion, at least one protruding portion 30, and the securing plate 17 at least one corresponding recess 31. Conversely, the protruding portion may be on the securing plate, in which case the recess will be on the fixation means. The protruding portion 30 and the recess 31 according to FIG. 4 take the form respectively of a longitudinal radial bulge and a corresponding longitudinal radial groove, but they may be of any shape appropriate to the purpose and may run otherwise than radially. The number of protruding portions 30 and corresponding recesses 31 may also vary as necessary and desired. Engagement of the protruding portion 30 in the recess 31 prevents or helps to prevent the fixation means 1 concerned from rotating relative to the securing plate 17 about its longitudinal axis CL, and/or the fixation means from changing its angular position relative to the securing plate and relative to other fixation means.

By a smooth middle portion 32, the fixation means 1 is configured to allow the bone fragments 2, 3 to be compressed so that the first bone fragment 2 slides inwards from the securing plate 17 towards the second bone fragment 3 in which the fixation means is anchored. On such occasions, the securing plate 17 will, through being locked to the fixation means 1, cease its abutment against the first bone fragment 2 (not depicted), but without affecting the strength of the connection and without any impairment of function.

It will be obvious to one skilled in the art that, beyond what is indicated above, the device according to the present invention can be modified and altered within the scope of the claims set out below without departing from the idea and objects of the invention. Thus, for example, the form and number of, and choice of material for, securing plates and securing means may vary as necessary and desired. In addition, the fixation means may, as indicated above, be other than bone nails comprising sleeves with pins.

The invention claimed is:

1. A device for fixation of bone fragments at bone fractures, which device comprises at least two fixation means (1), a securing plate (17), and a securing means (18) for the respective fixation means,
which fixation means (1) each have a first fixing portion (9) for fixing the fixation means (1) in an inner bone fragment (3), a second fixing portion (27, 30) for locking the fixation means (1), via the securing means (18), to the securing plate (17), the securing plate (17) being adapted to be disposed on the outside of an outer bone fragment (2) without a fixed connection with the outer bone fragment (2) and allowing movement of the outer bone fragment (2) relative to the securing plate (17), so that the fixation means (1) are prevented from changing their angular position relative to the securing plate (17) and relative to one another, and a middle portion (32) which is situated between the fixing portions (9, 27, 30) and is adapted to run through the outer bone fragment (2), the middle portion (32) being configured to allow the outer bone fragment (2), during secondary compression of the outer bone fragment (2) and the inner bone fragment (3), to (a) slide inwards along the middle portion (32) away from the securing plate (17) and towards the inner bone fragment (3) in which the fixation means (1) is fixed and (b) at the same time cease its abutment against the securing plate (17) in which the fixation means (1) is locked, thereby defining a space between said outer bone fragment (2) and said securing plate (17).

2. A device according to claim 1, in which said second fixing portion (27) of the respective fixation means (1); the securing means (18); and the securing plate (17) are configured to lock the fixation means (1) and the securing plate (17) by drawing the fixation means (1) firmly against the securing plate (17).

3. A device according to claim 1,
in which the respective securing means is a bone screw (18),
in which the securing plate (17) has holes (19) through which a threaded portion (20) of the respective bone screw (18) is inserted until a head (21) of the screw (18) abuts against the surface (22) of the securing plate (17), and
in which the said second fixing portion (27) of the respective fixation means (1) has a threaded hole (23) in which the threaded portion (20) of the bone screw (18) is screwed into such that the fixation means (1) is drawn towards the securing plate (17) until a rear surface (24) of the fixation means (1) abuts against a bearing surface (25) of the securing plate (17).

4. A device according to claim 3,
in which the securing plate (17) has a recess (26) for rear portions (27) of the respective fixation means (1) which constitute said second fixing portion,
in which a bottom of the respective recess (26) constitutes the bearing surface (25) against which the rear surface (24) of the fixation means (1) is tightenable, and
in which the diamter or equivalent of the respective recess (26) and the diameter or equivalent of the rear portions (27) of the respective fixation means (1) are mutually adapted so that said rear portions fit into the recess with substantially no play between them, and sidewalls (28) in the recess (26) substantially prevent the rear portions (27) of each of the fixation means (1), which engage in the recess (26), from changing their angular position relative to the securing plate (17) and relative to each other.

5. A device according to claim 4,
in which the respective fixation means (1), has at least one protruding portion (30) located on at least part of said second fixing portion (27), and the securing plate (17) has at least one corresponding recess (31) or vice versa, and
in which engagement of said protruding portion (30) in said recess (31) prevents or helps to prevent the fixation means (1) from rotating relative to the securing plate (17) about a longitudinal axis (CL), and/or each of the fixation means (1) from changing its angular position relative to the securing plate and relative to each other.

6. A device according to claim 5,
in which said protruding portion (30) and corresponding recess (31) run radially.

7. A device according to claim 1, in which each fixation means is a bone nail (1) which comprises a sleeve (5) and, disposed therein, a pin (7), the pin (7) moving in the sleeve so that at least one forward portion (9) of the pin (7) is driven outwards through at least one side aperture (13) in the sleeve (5), which forward portion (9) constitutes a first fixing portion in the form of at least one hook which engages in the inner bone fragment (3).

8. A device according to claim 7, in which the bone nail (1) is so configured or applied that, during the driving, the forward portion (9) of the pin (7) engages in the central portions of the inner bone fragment (3).

9. A device for fixation of bone fragments at bone fractures, comprising:
a securing plate (17) adapted to be disposed on the outside of an outer bone fragment (2);
at least two fixation means (1), each having a first portion (9) adapted to extend into an inner bone fragment (3), a second fixing portion (27, 30); and a middle portion (32) located between the first and second fixing portions (9; 27, 30) and adapted to extend through the outer bone fragment (2), the middle portion (32) allowing the outer bone fragment (2) to (a) slide inwards along the middle portion (32) away from the securing plate (17) and towards the inner bone fragment (3) and (b) at the same time cease its abutment against the securing plate (17); and
a securing means (18) locking the at least two fixation means (1) to the securing plate (17), the securing means (18) preventing the at least two fixation means (1) from changing angular positions relative to the securing plate (17) and relative to each other.

\* \* \* \* \*

UNITED STATES PATENT AND TRADEMARK OFFICE
CERTIFICATE OF CORRECTION

| | | |
|---|---|---|
| PATENT NO. | : 9,308,032 B2 | Page 1 of 1 |
| APPLICATION NO. | : 12/670147 | |
| DATED | : April 12, 2016 | |
| INVENTOR(S) | : Henrik Hansson | |

It is certified that error appears in the above-identified patent and that said Letters Patent is hereby corrected as shown below:

In the claims,

Column 5, claim 4, line 8, reads "diamter" should read -- diameter --

Signed and Sealed this
Seventh Day of June, 2016

Michelle K. Lee
*Director of the United States Patent and Trademark Office*